US012642620B2

(12) United States Patent
Kabaria et al.

(10) Patent No.: US 12,642,620 B2
(45) Date of Patent: Jun. 2, 2026

(54) BIORESORBABLE 3D PRINTED ADHESION BARRIERS

(71) Applicant: Carbon, Inc., Redwood City, CA (US)

(72) Inventors: Hardik Kabaria, Redwood City, CA (US); Eleanor R. Meyer, Portola Valley, CA (US); Steven Kenneth Pollack, Madison, WI (US)

(73) Assignee: Carbon, Inc., Redwood City, CA (US)

( * ) Notice: Subject to any disclaimer, the term of this patent is extended or adjusted under 35 U.S.C. 154(b) by 1246 days.

(21) Appl. No.: 17/518,990

(22) Filed: Nov. 4, 2021

(65) Prior Publication Data

US 2022/0142729 A1     May 12, 2022

Related U.S. Application Data

(60) Provisional application No. 63/110,450, filed on Nov. 6, 2020.

(51) Int. Cl.
| | |
|---|---|
| *A61B 90/00* | (2016.01) |
| *A61L 31/12* | (2006.01) |
| *A61L 31/14* | (2006.01) |
| *B33Y 80/00* | (2015.01) |

(52) U.S. Cl.
CPC ............ *A61B 90/08* (2016.02); *A61L 31/129* (2013.01); *A61L 31/148* (2013.01); *B33Y 80/00* (2014.12); *A61B 2090/0816* (2016.02); *Y10T 428/24058* (2015.01); *Y10T 428/24149* (2015.01); *Y10T 428/24273* (2015.01); *Y10T 428/24298* (2015.01)

(58) Field of Classification Search
CPC ............ A61B 90/08; A61B 2090/0816; A61L 31/129; A61L 31/148; B33Y 80/00; Y10T 428/24058; Y10T 428/24149; Y10T 428/24273; Y10T 428/24298; Y10T 428/24165
See application file for complete search history.

(56) References Cited

U.S. PATENT DOCUMENTS

| | | | | |
|---|---|---|---|---|
| 4,136,222 A | * | 1/1979 | Jonnes ...................... | B32B 3/12 428/116 |
| 5,039,567 A | * | 8/1991 | Landi .................. | B29C 66/1122 428/116 |
| 5,134,229 A | | 7/1992 | Saferstein et al. | |
| 5,906,997 A | * | 5/1999 | Schwartz .............. | A61L 31/145 514/56 |
| 6,150,581 A | * | 11/2000 | Jiang ...................... | A61K 45/06 602/50 |
| 6,251,419 B1 | * | 6/2001 | Graber .................. | A61L 31/048 424/435 |

(Continued)

FOREIGN PATENT DOCUMENTS

| | | | | |
|---|---|---|---|---|
| CA | 2962152 A1 | * | 9/2018 | .......... A61L 31/148 |

*Primary Examiner* — Donald M Flores, Jr.
(74) *Attorney, Agent, or Firm* — Myers Bigel, P.A.

(57) ABSTRACT

An adhesion barrier is comprised of, consists of, or consists essentially of a sheet having a top surface and a bottom surface. The sheet includes either (i) interconnected links or (ii) interconnected, vertically aligned, partitions. The links form pores or the partitions form pores, with the pores extending from the top surface through the bottom surface. The sheet is comprised of, consists of, or consists essentially of a flexible or elastic polymer.

25 Claims, 7 Drawing Sheets

(56) References Cited

U.S. PATENT DOCUMENTS

| 6,596,304 B1 * | 7/2003 | Bayon .................. A61L 15/325 |
| | | 435/395 |
| 6,599,526 B2 * | 7/2003 | Dimitrijevich ..... A61L 27/3804 |
| | | 424/443 |
| 6,743,521 B2 * | 6/2004 | Hubbell ................. A61K 47/34 |
| | | 428/688 |
| 6,869,938 B1 * | 3/2005 | Schwartz ............... C08L 1/286 |
| | | 536/51 |
| 7,144,588 B2 * | 12/2006 | Oray .................... A61L 31/005 |
| | | 424/548 |
| 7,491,408 B2 * | 2/2009 | Ogura ................... A61L 31/06 |
| | | 424/443 |
| 9,656,001 B2 | 5/2017 | Mayes et al. |
| 9,801,913 B2 | 10/2017 | Ferraro et al. |
| 10,213,530 B2 | 2/2019 | Saito et al. |
| 2005/0244455 A1 | 11/2005 | Greenawalt |
| 2008/0254091 A1 | 10/2008 | Lee et al. |
| 2008/0300691 A1 | 12/2008 | Romero-Ortega et al. |
| 2009/0018479 A1 * | 1/2009 | McCarthy ............... A61F 13/20 |
| | | 527/300 |
| 2012/0040137 A1 * | 2/2012 | Palasis ................. A61L 31/148 |
| | | 428/156 |
| 2013/0158651 A1 | 6/2013 | Hollister et al. |
| 2018/0117219 A1 | 5/2018 | Yang et al. |
| 2018/0299066 A1 * | 10/2018 | Erno ......................... F16S 5/00 |
| 2019/0167834 A1 | 6/2019 | Martin et al. |
| 2021/0178114 A1 * | 6/2021 | Brumlik ................. A44C 11/00 |
| 2022/0079280 A1 * | 3/2022 | Laperriere ............. B22F 10/10 |
| 2025/0307495 A1 * | 10/2025 | Liu ......................... G06F 30/23 |

* cited by examiner

BIORESORBABLE 3D PRINTED ADHESION BARRIERS

RELATED APPLICATIONS

This application claims priority from U.S. Provisional Patent Application No. 63/110,450, filed Nov. 6, 2020, the disclosure of which is hereby incorporated by reference in its entirety.

FIELD OF THE INVENTION

The present invention concerns surgical adhesion barriers and methods of making the same.

BACKGROUND OF THE INVENTION

Adhesions are internal scar tissue that forms between organs or tissues following surgery. Such adhesions can be painful, reduce movement, and where surgery must be repeated can severely complicate a subsequent surgery. Accordingly, there have been efforts to develop adhesion barriers that serve to reduce the incidence or severity of such adhesions.

A group of additive manufacturing techniques sometimes referred to as "stereolithography" creates a three-dimensional object by the sequential polymerization of a light polymerizable resin. Such techniques may be "bottom-up" techniques, where light is projected into the resin on the bottom of the growing object through a light transmissive window, or "top down" techniques, where light is projected onto the resin on top of the growing object, which is then immersed downward into the pool of resin.

The recent introduction of a more rapid stereolithography technique known as continuous liquid interface production (CLIP), coupled with the introduction of "dual cure" resins for additive manufacturing, has expanded the usefulness of stereolithography from prototyping to manufacturing (see, e.g., U.S. Pat. Nos. 9,211,678; 9,205,601; and U.S. Pat. No. 9,216,546 to DeSimone et al.; and also in J. Tumbleston, D. Shirvanyants, N. Ermoshkin et al., Continuous liquid interface production of 3D Objects, *Science* 347, 1349-1352 (2015); see also Rolland et al., U.S. Pat. Nos. 9,676,963, 9,453,142 and 9,598,606).

The application of additive manufacturing techniques such as CLIP to the production of adhesion barriers has not, however, been extensively explored.

SUMMARY OF THE INVENTION

Some embodiments of the present invention are directed to an adhesion barrier comprising, consisting of, or consisting essentially of a sheet having a top surface and a bottom surface. The sheet includes either (i) interconnected links or (ii) interconnected, vertically aligned, partitions. The links form pores or the partitions form pores, with the pores extending from the top surface through the bottom surface. The sheet is comprised of, consists of, or consists essentially of a flexible or elastic polymer.

In some embodiments: the sheet has a thickness of at least 0.1, 1, or 2 millimeters, up to 4 or 5 millimeters or more; the pores have an average diameter of at least 0.05, 0.1 or 0.5 millimeters, up to 1 or 2 millimeters or more; and/or the partitions when present have an average thickness of at least 0.1 or 0.2 millimeters, up to 0.5, 1, or 2 millimeters or more.

In some embodiments, the sheet is comprised of interconnected (optionally but in some embodiments preferably free-floating and independent) links. The links may be rectangular (e.g., include a pair of facing side elements optionally arranged as a square), pentagonal, hexagonal, round, or elliptical in shape. The links may include at least one internal bridge configured to reduce lateral compacting of said links.

In some embodiments, the sheet includes interconnected, vertically aligned, partitions. The partitions may be curved, planar, or a combination thereof.

The sheet may have a length (X) dimension, a width (Y) dimension, and a depth (or vertical) (Z) dimension, with the length and width dimensions together comprising lateral dimensions. The sheet may be stiffer in the vertical dimension than in the lateral dimensions (e.g., at least two or four times stiffer).

In some embodiments, the sheet is produced from a light polymerizable resin by an additive manufacturing process. The process may be or include bottom up or top down stereolithography.

In some embodiments, the polymer is or includes a bioresorbable polyester.

In some embodiments, the adhesion barrier is prepared by photopolymerization of a resin comprising or consisting essentially of: (a) from 5 or 10 percent by weight to 80 or 90 percent by weight of (meth)acrylate terminated bioresorbable polyester oligomer; (b) from 1 or 5 percent by weight to 50 or 70 percent by weight of non-reactive diluent; (c) from 0.1 or 0.2 percent by weight to 2 or 4 percent by weight of photoinitiator; (d) optionally, from 1 or 5 percent by weight to 40 or 50 percent by weight of reactive diluent; and (e) optionally, from 1 or 2 percent by weight to 40 or 50 percent by weight of filler.

In some embodiments, the oligomer includes a linear oligomer.

In some embodiments, the oligomer includes a branched oligomer (i.e., a star oligomer, such as a tri-arm oligomer).

In some embodiments, the oligomer includes degradable ester linkages between constituents selected from caprolactone, lactide, glycolide and dioxanone monomers in an ABA block, BAB block, CBC block, BCB block, AB random composition, BC random composition, or any combination thereof, wherein:

A=poly(lactide) (PLA), poly(glycolide) (PGA), or poly(lactide-co-glycolide) (PLGA), B=polycaprolactone (PCL), and C=polydioxanone (PDX).

In some embodiments, the oligomer has a molecular weight (Mn) of from 2, 5 or 10 kilodaltons to 10, 15 or 20 kilodaltons.

In some embodiments, the oligomer includes an ABA block or a CBC block in linear and/or branched (e.g., star or tri-arm) form.

In some embodiments, A is: (i) poly(lactide); (ii) poly(glycolide); (iii) poly(lactide-co-glycolide) containing lactide and glycolide in a molar ratio of either 90:10 to 55:45 lactide:glycolide (i.e., a lactide rich ratio) or 45:55 to 10:90 lactide:glycolide (i.e., a glycolide rich ratio); or any combination of the foregoing.

In some embodiments:

A (PLA, PGA, PLGA, or a combination thereof) has a molecular weight (Mn) of from 1,000 or 2,000 daltons, up to 4,000 or 10,000 daltons); and B (PCL) has a molecular weight (Mn) of from 1,000 or 1,600 daltons, up to 4,000 or 10,000 daltons.

In some embodiments, the non-reactive diluent is selected from the group consisting of dimethylformamide, dimethylacetamide, N-methyl pyrrolidone (NMP), dimethyl sulfoxide, cyclic carbonate (such as propylene carbonate), diethyl adipate, methyl ether ketone, ethyl alcohol, acetone, and combinations thereof.

In some embodiments, the non-reactive diluent is propylene carbonate.

In some embodiments, the reactive diluent includes an acrylate, a methacrylate, a styrene, a vinylamide, a vinyl ether, a vinyl ester, polymers containing any one or more of the foregoing, or a combination of two or more of the foregoing.

In some embodiments, the adhesion barrier and/or resin further includes at least one additional ingredient selected from: pigments, dyes, active compounds or pharmaceutical compounds, and detectable compounds (e.g., fluorescent, phosphorescent, radioactive), and combinations thereof.

In some embodiments, the adhesion barrier and/or resin further comprises a filler (e.g., bioresorbable polyester particles, sodium chloride particles, calcium triphosphate particles, sugar particles).

In some embodiments, the adhesion barrier is prepared by photopolymerization of a resin consisting essentially of:

(a) from 5 or 10 percent by weight to 80 or 90 percent by weight of a (meth)acrylate terminated, linear or branched, bioresorbable polyester oligomer of monomers in an ABA block or CBC block, wherein:

A is poly(lactide) (PLA), poly(glycolide) (PGA), poly(lactide-co-glycolide) (PLGA), or a combination thereof, with said PLGA containing lactide and glycolide in a molar ratio of either 90:10 to 60:40 lactide:glycolide (i.e., a lactide rich ratio) or 40:60 to 10:90 lactide:glycolide (i.e., a glycolide rich ratio), and A has a molecular weight (Mn) of from 1,000 or 2,000 daltons, up to 4,000 or 10,000 daltons);

B is polycaprolactone (PCL) and has a molecular weight (Mn) of from 1,000 or 1,600 daltons, up to 4,000 or 10,000 daltons; and C is polydioxanone (PDX) and has a molecular weight (Mn) of from 1,000 or 2,000 daltons, up to 4,000 or 10,000 daltons) and (b) from 1 or 5 percent by weight to 50 or 70 percent by weight of propylene carbonate;

(c) from 0.1 or 0.2 percent by weight to 2 or 4 percent by weight of photoinitiator, (d) optionally, from 1 or 5 percent by weight to 40 or 50 percent by weight of reactive diluent; and (e) optionally, from 1 or 2 percent by weight to 40 or 50 percent by weight of filler.

In some embodiments, the adhesion barrier is produced by photopolymerizing a resin in the shape of the adhesion barrier (e.g., by additive manufacturing, such as by bottom-up or top-down additive manufacturing).

In some embodiments, the resin is a resin as described herein.

Some other embodiments of the present invention are directed to a method of making an adhesion barrier as described herein, including producing the adhesion barrier by photopolymerizing a resin as described herein in the shape of the adhesion barrier (e.g., by additive manufacturing, such as by bottom-up or top-down additive manufacturing).

In some embodiments, the method includes exposing the adhesion barrier to additional light after the producing step to further react unpolymerized constituents therein.

In some embodiments, the method includes cleaning the adhesion barrier (e.g., by washing, wiping, spinning, etc.) after the producing step (but preferably before the step of exposing the adhesion barrier to additional light).

In some embodiments, the method includes extracting residual diluent from the adhesion barrier after said producing step.

In some embodiments, the method includes drying the adhesion barrier (optionally but preferably under a vacuum) to remove extraction solvents therefrom.

In some embodiments, the method includes producing the adhesion barrier in enlarged form to offset shrinkage of the adhesion barrier that occurs during the extracting, further exposing, and/or cleaning steps, and drying steps.

The foregoing and other objects and aspects of the present invention are explained in greater detail in the drawings herein and the specification set forth below. The disclosures of all United States patent references cited herein are to be incorporated herein by reference.

DETAILED DESCRIPTION

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations of one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly-used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

The transitional phrase "consisting essentially of" means that the scope of a claim is to be interpreted to encompass the specified materials or steps recited, and also additional materials or steps that do not materially affect the basic and novel characteristics of the claimed invention as described herein.

The disclosures of all patent references cited herein are to be incorporated herein by reference in their entirety.

1. Adhesion Barrier Structures.

Figure 1:
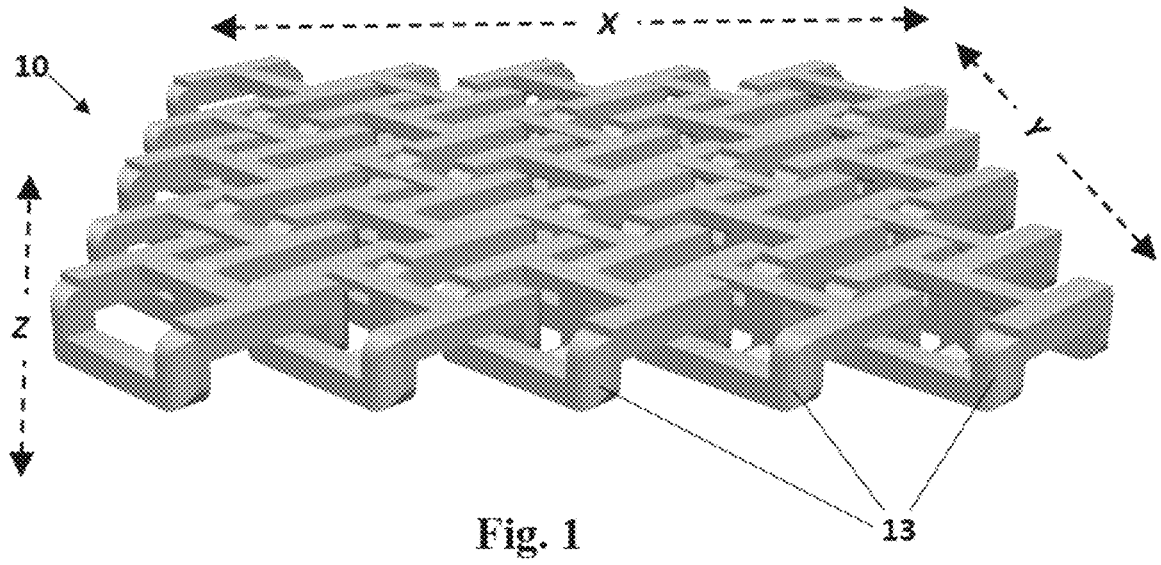
FIG. 1 is a perspective view of an adhesion barrier as described herein, comprised of interconnected links.
Figure 2:
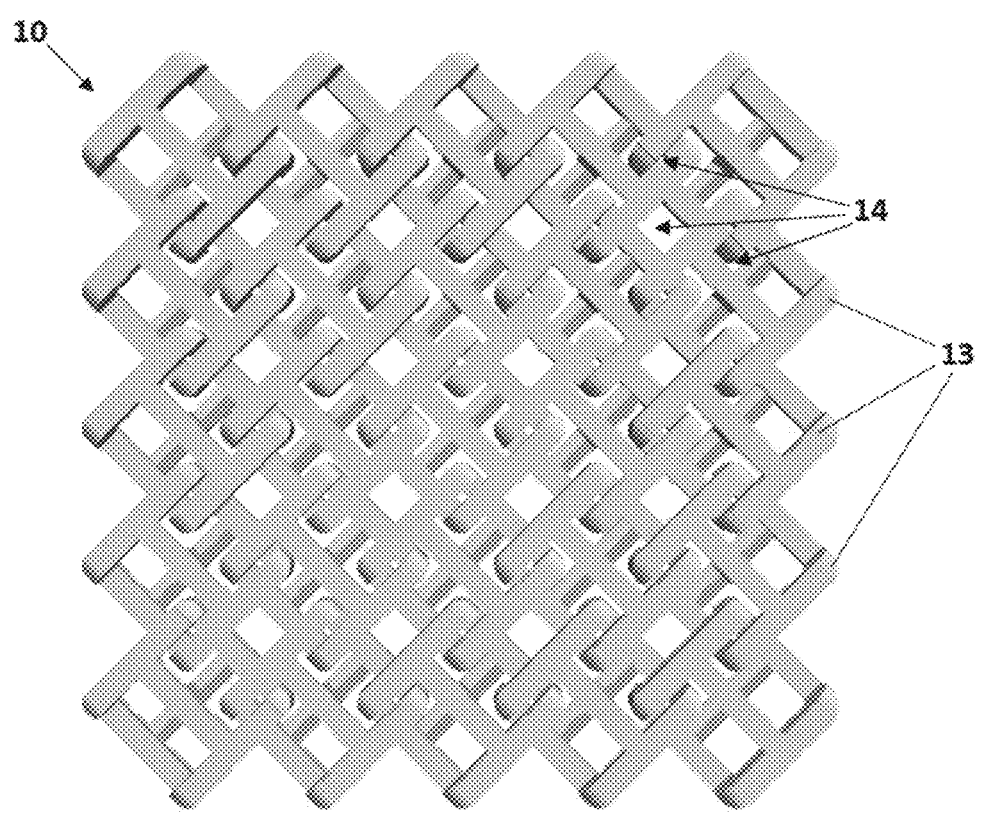
FIG. 2 is a plan view of the adhesion barrier of FIG. 1.
Figure 3:
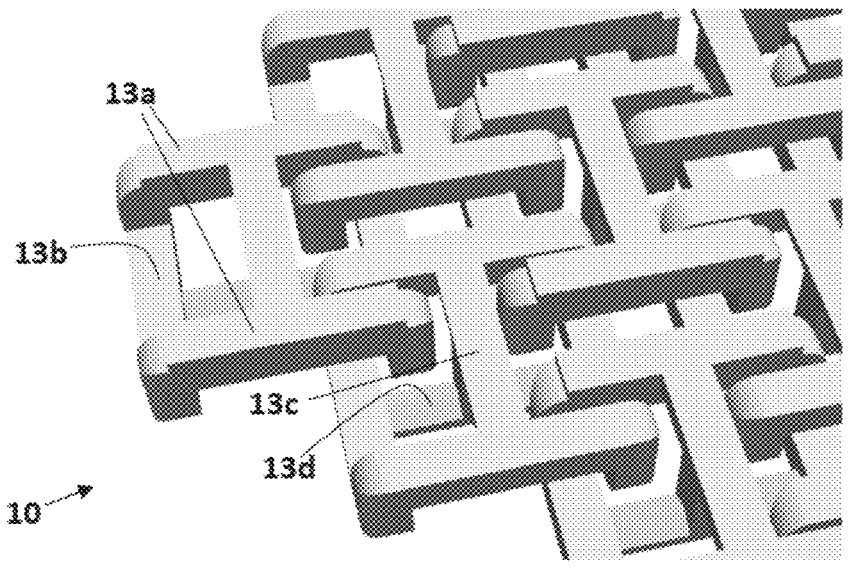
FIG. 3 is a detail perspective view of the adhesion barrier of FIGS. 1-2.
Figure 4:
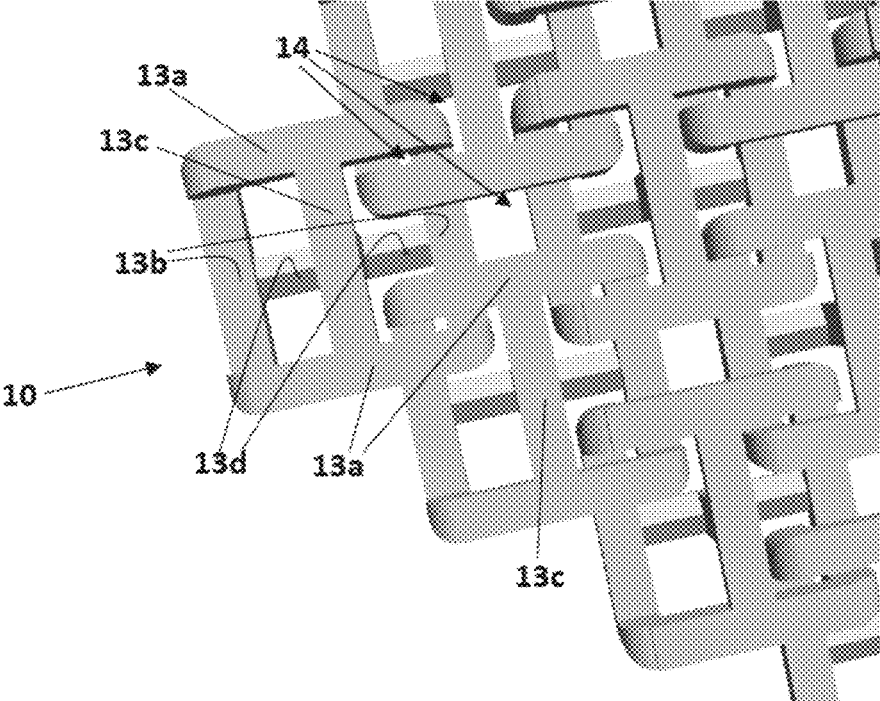
FIG. 4 is a detailed plan view of the adhesion barrier of FIGS. 1-3.
Figure 5:
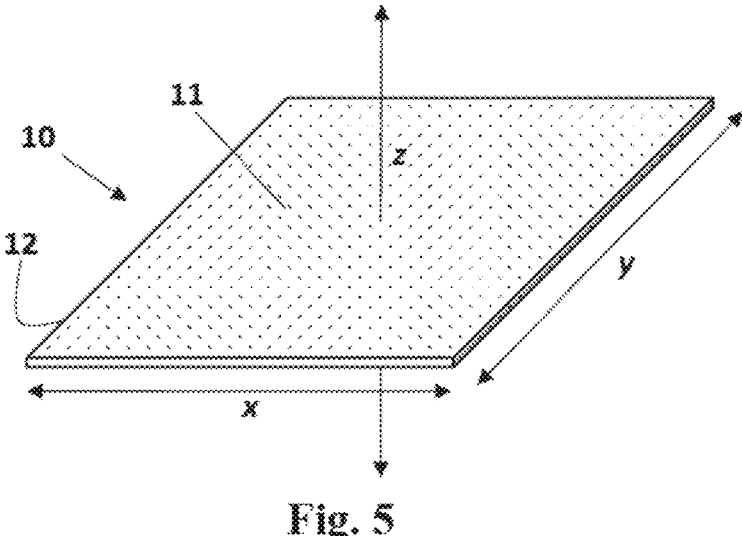
FIG. 5 is a schematic perspective view of an adhesion barrier as described herein, labelling the X, Y, and Z axes.
Figure 6:
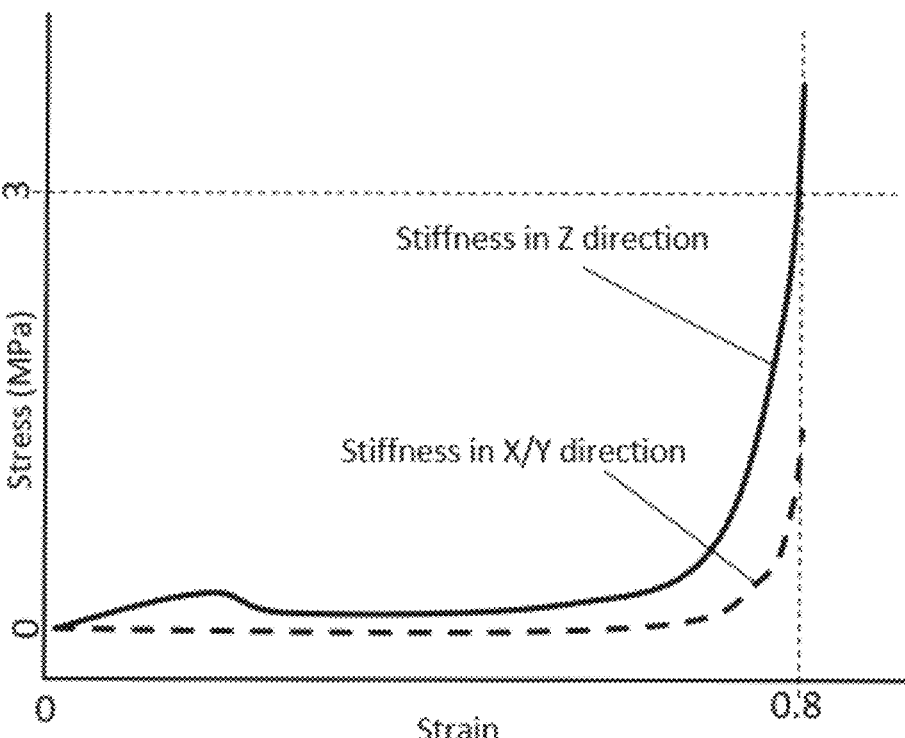
FIG. 6 shows representative stress-strain curves for an adhesion barrier as described herein, in the X/Y direction, and in the Z direction.
Figure 7B:
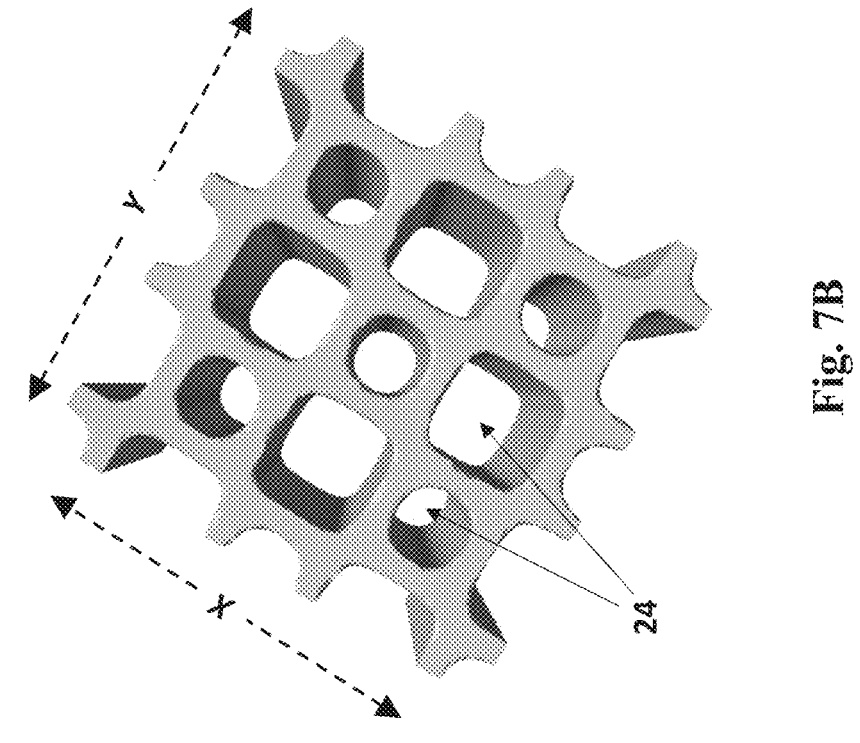
FIG. 7B is a plan view of the sheet portion of FIG. 7A.
Figure 7A:
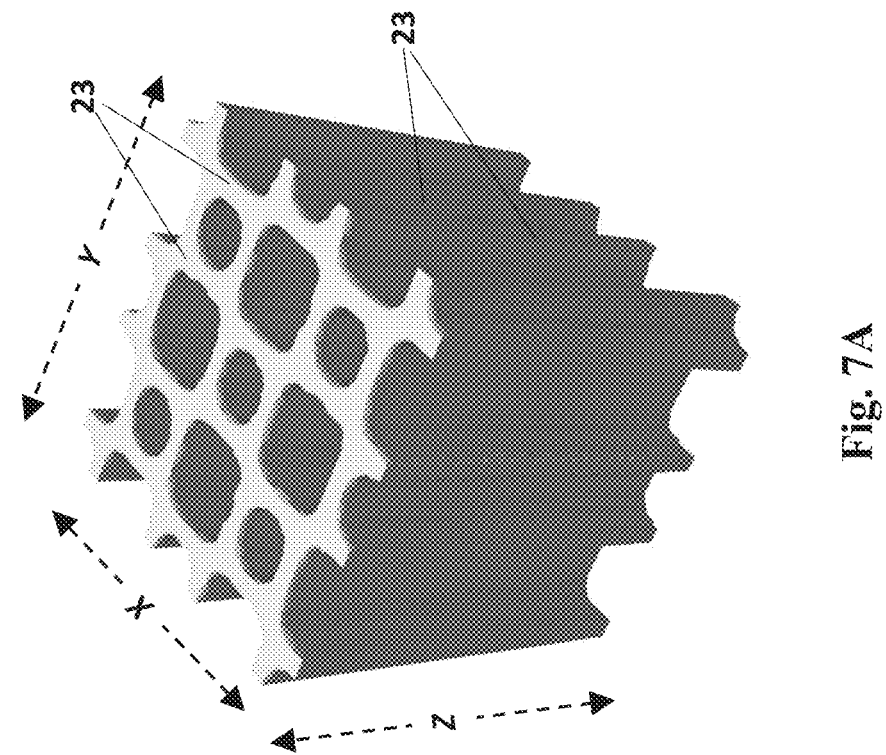
FIG. 7A is a perspective view of a portion of the sheet of an adhesion barrier as described herein.
Figures 8A, 8B:
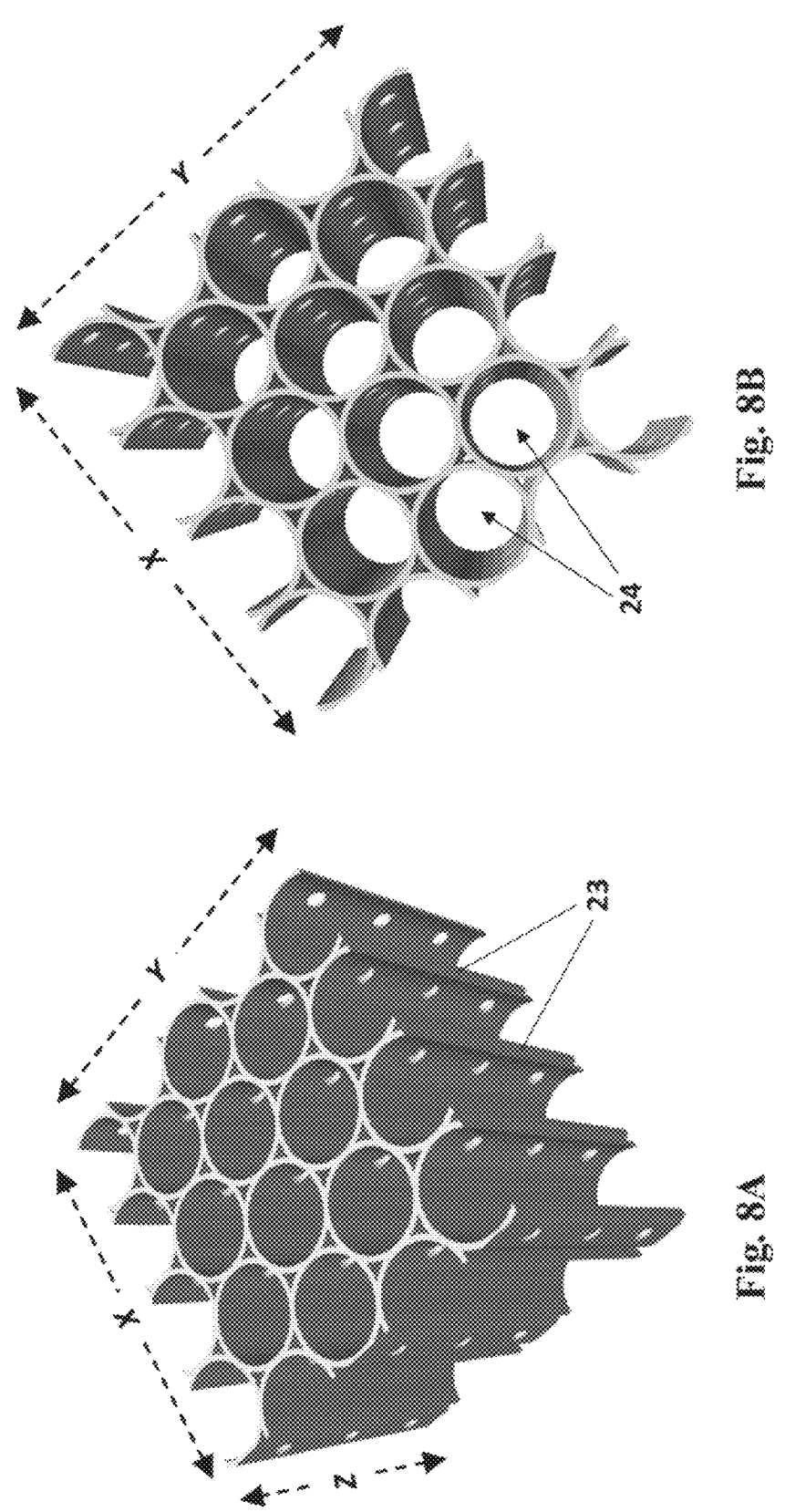
FIG. 8A is a perspective view of an alternate portion of the sheet of an adhesion barrier as described herein.
FIG. 8B is a plan view of the sheet portion of FIG. 8A.
Figure 9B:
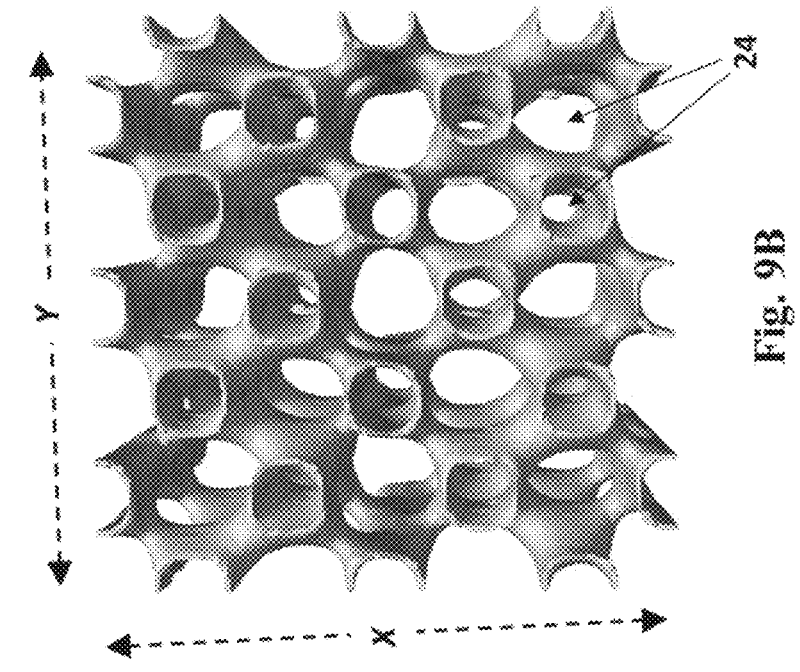
FIG. 9B is a plan view of the sheet portion of FIG. 9A.
Figure 9A:
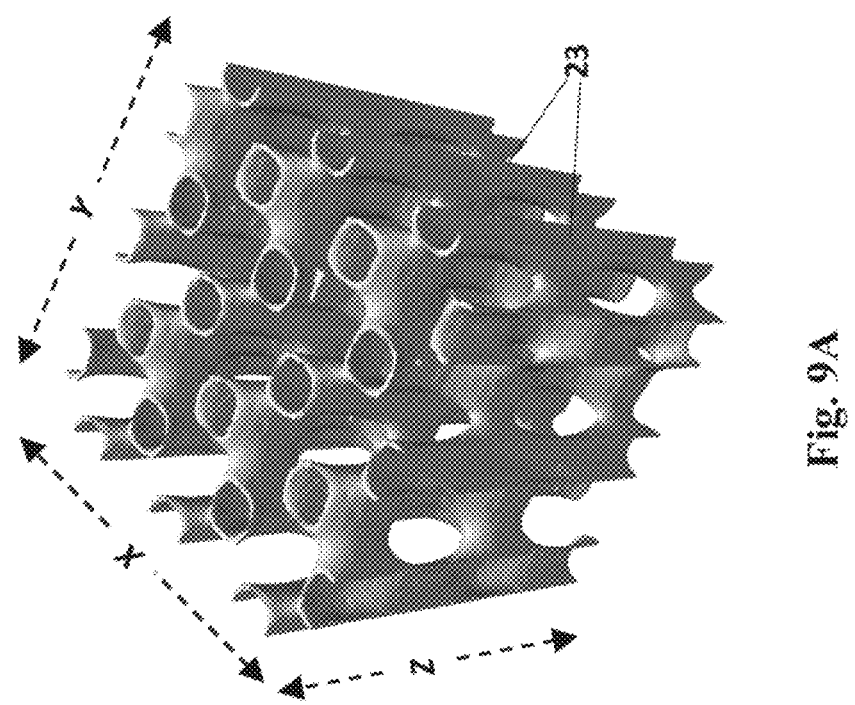
FIG. 9A is a perspective view of an alternate portion of the sheet for an adhesion barrier as described herein.
Figures 10A, 10B:
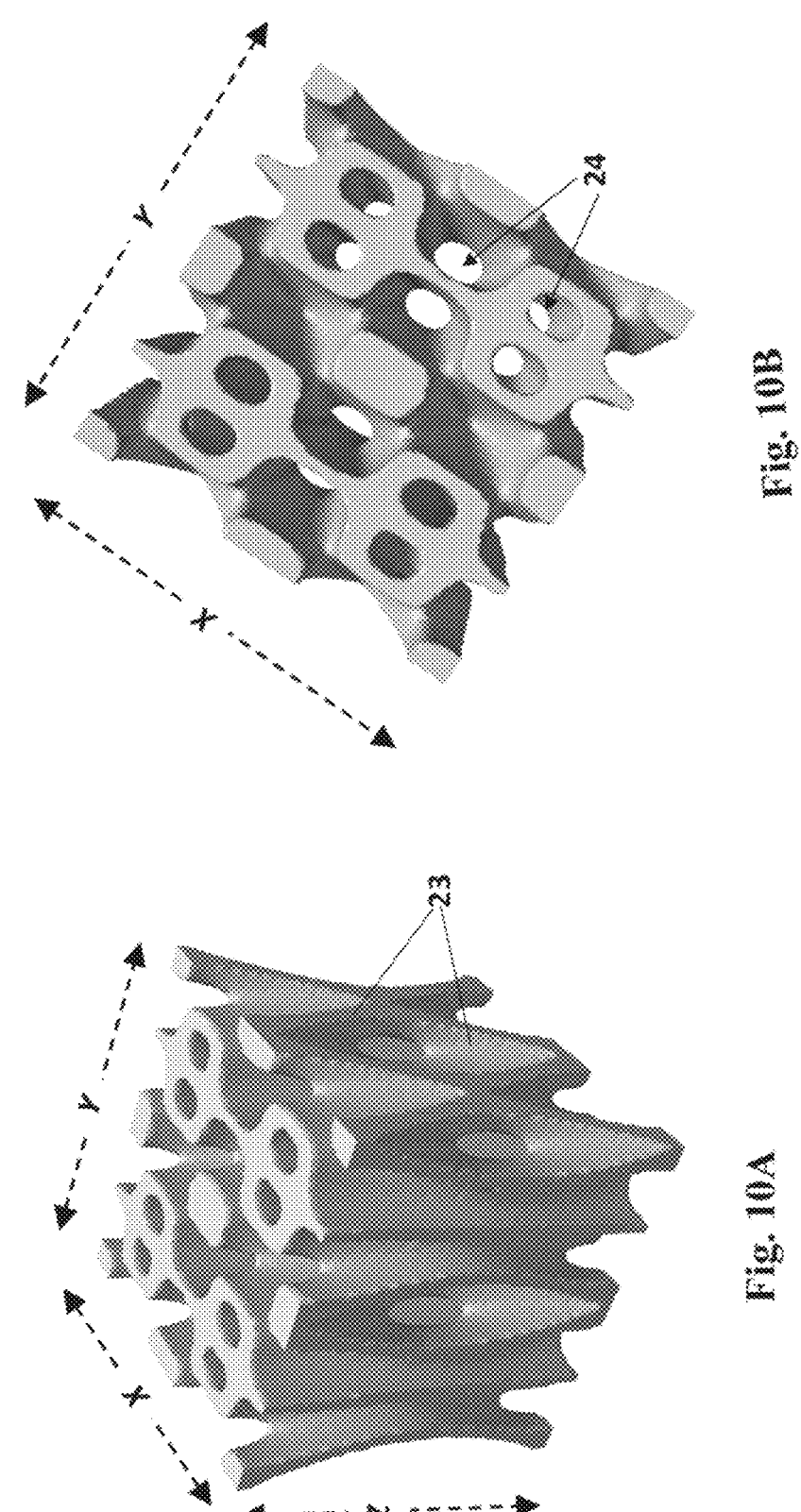
FIG. 10A is a perspective view of an alternate portion of the sheet for an adhesion barrier as described herein.
FIG. 10B is a plan view of the sheet portion of FIG. 10A.

Referring to FIGS. 1-5, an adhesion barrier comprises, consists of, or consists essentially of a sheet 10 having a top surface 11 and an opposite bottom surface 12. The sheet includes either (i) interconnected links 13 or (ii) interconnected, vertically aligned, partitions 23 (FIGS. 7-10). The links 13 define or form pores 14 or the partitions 23 define or form pores 24. The pores extend between the top surface 11 and the bottom surface 12. The sheet 10 is comprised of, consists of, or consists essentially of a flexible or elastic polymer.

The sheet 10 may have a thickness of at least 0.1, 1, or 2 millimeters, up to 4 or 5 millimeters or more. The pores 14 or 24 may have an average diameter of at least 0.05, 0.1 or 0.5 millimeters, up to 1 or 2 millimeters or more. The partitions 23 when present may have an average thickness of at least 0.1 or 0.2 millimeters, up to 0.5, 1, or 2 millimeters or more.

The sheet 10 may be comprised of interconnected links 13. The links 13 are optionally but in some embodiments preferably free-floating and independent.

The links 13 may be rectangular, e.g., including first and second pair of facing side elements or members 13a, 13b, optionally arranged as a square. The elements 13a, 13b may be perpendicular to one another. There may be at least one internal bridge 13c, 13d configured to reduce lateral compacting of the links. The (first) internal bridge 13c may extend between the first pair of facing side members 13a and may be perpendicular thereto. The (second) internal bridge 13d may extend between the second pair of facing side members 13b and may be perpendicular thereto. In some other embodiments, the links 13 may be pentagonal, hexagonal, round, or elliptical in shape.

In some embodiments, the sheet 10 includes interconnected, vertically aligned, partitions 23 (FIGS. 7-10). The partitions may be curved, planar, or a combination thereof.

The sheet 10 has a length (X) dimension, a width (Y) dimension, and a depth (or vertical) (Z) dimension, with length and width dimensions together comprising lateral dimensions. The sheet is stiffer in the vertical dimension than in the (one or both) lateral dimensions (e.g., at least two or four times stiffer).

The sheet 10 may be produced from a light polymerizable resin by an additive manufacturing process. The process may include bottom up or top down stereolithography.

In some embodiments, the polymer is or includes a bioresorbable polyester.

2. Polymer Materials and Resins.

Resins useful for carrying out the present invention generally comprise, consist of, or consist essentially of:

(a) from 5 or 10 percent by weight to 80 or 90 percent by weight of (meth)acrylate terminated bioresorbable polyester oligomer;

(b) from 1 or 5 percent by weight to 50 or 70 percent by weight of non-reactive diluent;

(c) from 0.1 or 0.2 percent by weight to 2 or 4 percent by weight of photoinitiator;

(d) optionally, from 1 or 5 percent by weight to 40 or 50 percent by weight of reactive diluent;

(e) optionally, from 1 or 2 percent by weight to 40 or 50 percent by weight of filler; and (f) optionally, from 0.1 or 1 percent by weight to 10 or 20 percent by weight of additional ingredients such as an active agent, detectable group, pigment or dye, or the like.

Oligomer prepolymers for resins from which the polymers may be produced may be linear or branched (e.g., "star" oligomers such as tri-arm oligomers). Suitable end groups for such monomers or oligomer prepolymers include, but are not limited to, acrylate, methacrylate, fumarate, vinyl carbonate, methyl ester, ethyl ester, etc. Non-limiting examples of suitable resin compositions are given in Table 1 below (where constituents in each column can be combined with constituents of the other columns in any combination).

TABLE 1

| Backbone Chemistry | Reactive End Group | Oligomer Architecture | Plasticizer | Diluent | Photo-initiator |
|---|---|---|---|---|---|
| PLGA | Methacrylate | Linear | HO—PCL—OH | Mono-vinyl ether | Irgacure ® 2959 |
| PCL | Acrylate | Star (branching) | HO—PLGA—PCL—PLGA—OH | DEGMA | Irgacure ® TPO |
| PLGA—PCL—PLGA | Vinyl Carbonate | | | Vinyl acetate | ITX |
| PLGA—PEG—PLGA | Fatty acid methyl ester | | | n-butyl methacrylate | Irgacure ® 819 |
| PLGA—PCL | | | | Triacetine | |
| | | | | NMP | |
| | | | | DMSO | |

PLGA = poly(lactic-co-glycolic acid); PEG = polyethylene glycol; PCL = polycaprolactone; DEGMA = Di(ethylene glycol) methyl ether methacrylate; TPO = diphenyl (2,4,6-trimethylbenzoyl) phosphine oxide; ITX = isopropylthioxanthone; NMP = N-methyl pyrrolidone; DMSO = dimethylsulfoxide.

A particular example of a composition for use in producing the objects described herein is based on a methacrylate terminated oligomer with a bioresorbable polyester linkage, which provides rubber-like elastic behavior at physiological temperatures, short-term retention of mechanical properties (in some embodiments, 1 month or less), and long-term full resorption (in some embodiments, over a time of approximately 4-6 months).

Bioresorbable polyester oligomers for use in some preferred embodiments are, in general, bioresorbable oligomers with methacrylate end-groups. Such oligomers are typically comprised of degradable ester linkages selected from caprolactone, lactide, glycolide and dioxanone monomers in an ABA block, BAB block, CBC block, BCB block, AB random composition, BC random composition, or any combination thereof, where: A=poly(lactide) (PLA), poly(glycolide) (PGA), or poly(lactide-co-glycolide) (PLGA), B=polycaprolactone (PCL) and C=polydioxanone (PDX). Copolymers may have a molecular weight (Mn) of from 2, 5 or 10 kilodaltons to 10, 15 or 20 kilodaltons, in either linear or star structure. Monomers used to produce such oligomers may optionally introduce branches, such as to enhance elasticity, as is known in the art, an example being gamma-methyl-epsilon caprolactone and gamma-ethyl-epsilon-caprolactone.

In some embodiments, the oligomer comprises an ABA block or a CBC block in linear and/or branched (e.g., star or tri-arm) form.

In some embodiments, A is: (i) poly(lactide); (ii) poly (glycolide); (iii) poly(lactide-co-glycolide) containing lactide and glycolide in a molar ratio of either 90:10 to 55:45 lactide:glycolide (i.e., a lactide rich ratio) or 45:55 to 10:90 lactide:glycolide (i.e., a glycolide rich ratio); or any combination thereof.

In some embodiments, A (PLA, PGA, PLGA, or a combination thereof) has a molecular weight (Mn) of from 1,000 or 2,000 daltons, up to 4,000 or 10,000 daltons); and B (PCL) has a molecular weight (Mn) of from 1,000 or 1,600 daltons, up to 4,000 or 10,000 daltons.

A particular embodiment is a resin consisting essentially of: (a) from 5 or 10 percent by weight to 80 or 90 percent by weight of a (meth)acrylate terminated, linear or branched, bioresorbable polyester oligomer of monomers in an ABA block or CBC block, wherein: A is poly(lactide) (PLA), poly(glycolide) (PGA), poly(lactide-co-glycolide) (PLGA), or a combination thereof, with said PLGA containing lactide and glycolide in a molar ratio of either 90:10 to 60:40 lactide:glycolide (i.e., a lactide rich ratio) or 40:60 to 10:90 lactide:glycolide (i.e., a glycolide rich ratio), and A has a molecular weight (Mn) of from 1,000 or 2,000 daltons, up to 4,000 or 10,000 daltons; B is polycaprolactone (PCL) and has a molecular weight (Mn) of from 1,000 or 1,600 daltons, up to 4,000 or 10,000 daltons; and C is polydioxanone (PDX) and has a molecular weight (Mn) of from 1,000 or 2,000 daltons, up to 4,000 or 10,000 daltons; (b) from 1 or 5 percent by weight to 50 or 70 percent by weight of propylene carbonate; (c) from 0.1 or 0.2 percent by weight to 2 or 4 percent by weight of photoinitiator, (d) optionally, from 1 or 5 percent by weight to 40 or 50 percent by weight of reactive diluent; and (e) optionally, from 1 or 2 percent by weight to 40 or 50 percent by weight of filler.

Non-reactive diluents that can be used in carrying out the invention include, but are not limited to, dimethylformamide, dimethylacetamide, N-methyl pyrrolidone (NMP), dimethyl sulfoxide, cyclic carbonate (for example, propylene carbonate), diethyl adipate, methyl ether ketone, ethyl alcohol, acetone, and combinations of two or more thereof.

Photoinitiators included in the polymerizable liquid (resin) can be any suitable photoiniator, including type I and type II photoinitiators and including commonly used UV photoinitiators, examples of which include but are not limited to acetophenones (diethoxyacetophenone for example), phosphine oxides such as diphenyl(2,4,6-trimethylbenzoyl)phosphine oxide, phenylbis(2,4,6-trimethylbenzoyl) phosphine oxide (PPO), Irgacure® 369, etc. See, e.g., U.S. Pat. No. 9,453,142 to Rolland et al.

Reactive diluents that can be used in carrying out the invention can include an acrylate, a methacrylate, a styrene, a vinylamide, a vinyl ether, a vinyl ester, polymers containing any one or more of the foregoing, and combinations of one or more of the foregoing (e.g., acrylonitrile, styrene, divinyl benzene, vinyl toluene, methyl acrylate, ethyl acrylate, butyl acrylate, methyl (meth)acrylate, isobornyl acrylate (IBOA), isobornyl methacrylate (IBOMA), an alkyl ether of mono-, di- or triethylene glycol acrylate or methacrylate, a fatty alcohol acrylate or methacrylate such as lauryl (meth)acrylate, and mixtures thereof).

The resin can have additional ingredients therein, including pigments, dyes, diluents, active compounds or pharmaceutical compounds, detectable compounds (e.g., fluorescent, phosphorescent, radioactive), etc., again depending upon the particular purpose of the product being fabricated. Examples of such additional ingredients include, but are not limited to, proteins, peptides, nucleic acids (DNA, RNA) such as siRNA, sugars, small organic compounds (drugs and drug-like compounds), etc., including combinations thereof.

Fillers. Any suitable filler may be used in connection with the present invention, including but not limited to bioresorbable polyester particles, sodium chloride particles, calcium triphosphate particles, sugar particles, etc.

Dyes/non-reactive light absorbers. In some embodiments, resins for carrying out the present invention include a non-reactive pigment or dye that absorbs light, particularly UV light. Suitable examples of such light absorbers include, but are not limited to: (i) titanium dioxide (e.g., included in an amount of from 0.05 or 0.1 to 1 or 5 percent by weight), (ii) carbon black (e.g., included in an amount of from 0.05 or 0.1 to 1 or 5 percent by weight), and/or (iii) an organic ultraviolet light absorber such as a hydroxybenzophenone, hydroxyphenylbenzotriazole, oxanilide, benzophenone, thioxanthone, hydroxyphenyltriazine, and/or benzotriazole ultraviolet light absorber (e.g., Mayzo BLS1326) (e.g., included in an amount of 0.001 or 0.005 to 1, 2 or 4 percent by weight). Examples of suitable organic ultraviolet light absorbers include, but are not limited to, those described in U.S. Pat. Nos. 3,213,058; 6,916,867; 7,157,586; and 7,695, 643, the disclosures of which are incorporated herein by reference.

3. Methods of Making.

Additive manufacturing. Suitable additive manufacturing apparatus and methods on which objects can be produced include bottom-up and top-down additive manufacturing methods and apparatus, as known and described in, for example, U.S. Pat. No. 5,236,637 to Hull, U.S. Pat. Nos. 5,391,072 and 5,529,473 to Lawton, U.S. Pat. No. 7,438,846 to John, U.S. Pat. No. 7,892,474 to Shkolnik, U.S. Pat. No. 8,110,135 to El-Siblani, U.S. Patent Application Publication No. 2013/0292862 to Joyce, and US Patent Application Publication No. 2013/0295212 to Chen et al. The disclosures of these patents and applications are incorporated by reference herein in their entirety.

In some embodiments, the additive manufacturing step is carried out by one of the family of methods sometimes referred to as continuous liquid interface production (CLIP). CLIP is known and described in, for example, U.S. Pat. Nos. 9,211,678; 9,205,601; 9,216,546; and others; in J. Tumbleston et al., Continuous liquid interface production of 3D Objects, *Science* 347, 1349-1352 (2015); and in R. Janusziewcz et al., Layerless fabrication with continuous liquid interface production, *Proc. Natl. Acad. Sci. USA* 113, 11703-11708 (2016). Other examples of methods and apparatus for carrying out particular embodiments of CLIP include, but are not limited to: Batchelder et al., US Patent Application Pub. No. US 2017/0129169; Sun and Lichkus, PLGA is a random copolymer of lactide (L) and glycolide (G) with an L:G weight ratio of 1:1.

Refer to Table 2 for an example of the molar ratios and masses of each reagent used for a 1 kg batch of HO-PLGA-b-PCL-b-PLGA-OH synthesis as the next two sections are discussed.

TABLE 2

Example of molar ratios and mass of each reagent needed to synthesize a 1 kg batch of HO-PLGA-b-PCL-b-PLGA-OH.

| Reagent | Molecular Weight (g/mol) | Molar Ratio | Density (g/mol) | Mass (g) | Volume (mL) | Moles |
|---|---|---|---|---|---|---|
| Caprolactone (CL) | 114.14 | 22 | 1.03 | 400.0 | 388.4 | 3.50 |
| Diethylene glycol (DEG) | 106.12 | 1 | 1.12 | 16.9 | 15.1 | 0.16 |
| Stannous Octoate (Sn(Oct)) | 405.12 | $2.38 \times 10^{-3}$ | 1.25 | 0.15 | 0.12 | $3.81 \times 10^{-4}$ |
| D,L-Lactide (L) | 144.13 | 14 | — | 321.4 | — | 2.22 |
| Glycolide (G) | 116.07 | 14 | — | 258.8 | — | 2.22 |

US Patent Application Pub. No. US 2016/0288376; Willis et al., US Patent Application Pub. No. US 2015/0360419; Lin et al., US Patent Application Pub. No. US 2015/0331402; D. Castanon, US Patent Application Pub. No. US 2017/0129167; L. Robeson et al., PCT Patent Pub. No. WO 2015/164234 (see also U.S. Pat. Nos. 10,259,171 and 10,434,706): C. Mirkin et al., PCT Patent Pub, No, WO 2017/210298 (see also US Pat. App. US 2019/0160733). B. Feller, US Pat App. Pub. No. US 2018/0243976 (published Aug. 30, 2018); M. Panzer and J. Tumbleston, US Pat App Pub. No. US 2018/0126630 (published May 10, 2018); and K. Willis and B. Adzima, US Pat App Pub. No. US 2018/0290374 (Oct. 11, 2018).

Post-production steps. After the additive manufacturing steps, additional post processing steps can include washing (e.g., in an organic solvent such as acetone, isopropanol, a glycol ether such as dipropylene glycol methyl ether or DPM), wiping (e.g., with an absorbent material, blowing with a compressed gas or air blade, etc.) centrifugal separation of residual resin, extraction of residual solvents, additional curing such as by flood exposure with ultraviolet light or the like, drying said object (optionally but preferably under a vacuum) to remove extraction solvents therefrom, and combinations of some or all of the foregoing, in accordance with known techniques.

Additional resins and processes. While the present invention is described primarily in connection with the bioerodable polyester resins described above, it will be appreciated that, for some embodiments, any of a variety of single or dual cure resins can be used, including but not limited to those set forth in U.S. Pat. No. 9,205,601 to DeSimone et al. and U.S. Pat. No. 9,676,963 to Rolland et al.

The present invention is explained in greater detail in the following non-limiting Examples.

Examples 1-3

Preparation of a Difunctional Methacrylate (MA) Terminated Polyester Oligomer These examples describe the preparation of a difunctional, methacrylate terminated, polyester oligomer. The midblock is PLGA-PCL-PLGA, the molecular weight is 6 kilodaltons, and PCL is included as 40 wt % of the total MW.

Example 1

HO-PCL-OH Synthesis

A round bottom flask was dried in a drying oven overnight and cooled under $N_2$ flow to room temperature. Caprolactone and tin octoate were added to the round bottom flask via a glass syringe and syringe needle. The reaction flask contents were heated to 130° C. Meanwhile, diethylene glycol was heated to 130° C. Once preheated, diethylene glycol was added to the reaction flask as an initiator and was allowed to react until complete monomer conversion. Monomer conversion was monitored using $H^1$ NMR. The reaction was stopped, and the reaction contents were allowed to cool to room temperature. The HO-PCL-OH was precipitated into cold MeOH from chloroform to obtain a white solid. $H^1$ NMR, DSC, FTIR, and THF GPC were used to characterize HO-PCL-OH.

Example 2

HO-PLGA-b-PCL-b-PLGA-OH Synthesis

HO-PCL-OH and varying amounts of D,L-lactide and glycolide were added into a round-bottom flask under $N_2$ and heated to 140° C. to melt the reaction contents. After melting, the temperature was reduced to 120° C. and stannous octoate was added. The reaction continued with stirring while monitoring the monomer conversion with $H^1$ NMR and THF GPC. Once the reaction reaches the desired molecular weight, reaction contents were cooled to room temperature, dissolved in chloroform and precipitated into cold diethyl ether three times. The precipitate was dried under vacuum.

Example 3

MA-PLGA-b-PCL-b-PLGA-MA Synthesis

Refer to Table 3 for an example of the molar ratio and masses of each reagent used to synthesize a 1 kg batch of MA-PLGA-b-PCL-b-PLGA-MA.

TABLE 3

Example of molar ratios and mass of each reagent needed to synthesize a 1 kg
batch of MA-PLGA-b-PCL-b-PLGA-MA.

| Reagent | Molecular Weight (g/mol) | Molar Ratio | Density (g/mol) | Mass (g) | Volume (mL) | Moles |
|---|---|---|---|---|---|---|
| HO-PLGA-b-PCL-b-PLGA-OH | 6000 | 1 | — | 1000 | — | 0.17 |
| Methacrylol Chloride (MC) | 104.54 | 3.8 | 1.07 | 66.2 | 61.9 | 0.63 |
| Triethylamine (TEA) | 101.19 | 3.8 | 0.726 | 64.1 | 88.3 | 0.63 |
| Butylated hydroxy-toluene (BHT) | 220.35 | ~400 ppm | | 0.45 | | |
| Dichloromethane (DCM) | — | 0.2 g/mL | — | — | 5000 | — |

HO-PLGA-b-PCL-b-PLGA-OH was dissolved in anhydrous DCM in a round bottom flask under $N_2$. Triethylamine and a small amount BHT were added the reaction flask and the reaction flask was cooled to 0° C. in an ice water bath. The reaction flask was equipped with a pressure-equalizing addition funnel that was charged with methacrylol chloride. Once the reaction flask reached 0° C., methacrylol chloride was added dropwise over 2 hours. The reaction proceeded for 12 h at 0° C. and then 24 h at room temperature. Once complete, the reaction contents were washed with distilled water 2 times to remove the triethylamine hydrochloride salts, saturated $Na_2CO_3$, and dried over magnesium sulfate. The collected and dried DCM layer was dried with rotary evaporation. The final product was characterized with THF GPC, $H^1$ NMR, FTIR, and DSC.

Examples 4-6

Preparation of a Tri-Arm MA Terminated Polyester Oligomer

These examples describe the preparation of a tri-arm, or star shaped, bioresorbable polyester oligomer. Each arm is terminated with methacrylate. Each arm has a molecular weight of 2 kilodaltons and is a block copolymer of poly(lactide-r-glycolide) (PLGA) and poly(caprolactone) (PCL) with PCL being the core of the oligomer. The PCL is included as 40 wt % of the total MW. The PLGA is a random copolymer of lactide (L) and glycolide (G) with L:G weight ratio of 1:1.

Example 4

PCL-3OH Synthesis

Refer to Table 4 for an example of the molar ratios and masses of each reagent used for a 1 kg batch of (PLGA-b-PCL)-3OH synthesis as the next two sections are discussed.

TABLE 4

Example of molar ratios and mass of each reagent needed to synthesize a 1 kg
batch of (PCL-b-PLGA)-3OH.

| Reagent | Molecular Weight (g/mol) | Molar Ratio | Density (g/mol) | Mass (g) | Volume (mL) | Moles |
|---|---|---|---|---|---|---|
| Caprolactone (CL) | 114.14 | 22 | 1.03 | 400.0 | 388.4 | 3.50 |
| Trimethylolpropane (DEG) | 134.07 | 1 | 1.08 | 21.4 | 19.8 | 0.16 |
| Stannous Octoate (Sn(Oct)) | 405.12 | $2.38 \times 10^{-3}$ | 1.25 | 0.15 | 0.12 | $3.81 \times 10^{-4}$ |
| D,L-Lactide (L) | 144.13 | 14 | — | 321.4 | — | 2.22 |
| Glycolide (G) | 116.07 | 14 | — | 258.8 | — | 2.22 |

A round bottom flask was dried in a drying oven overnight and cooled under N2 flow to room temperature. Caprolactone and tin octoate were added to the round bottom flask via a glass syringe and syringe needle. The reaction flask contents were heated to 130° C. Meanwhile, trimethylolpropane (TMP) was heated to 130° C. Once preheated, TMP was added to the reaction flask as an initiator and was allowed to react until complete monomer conversion. Monomer conversion was monitored using H1 NMR. The reaction was stopped, and the reaction contents were allowed to cool to room temperature. The (PCL)-3OH was precipitated into cold MeOH from chloroform to obtain a white solid. H1 NMR, DSC, FTIR, and THF GPC were used to characterize (PCL)-3OH.

Example 5

(PCL-b-PLGA)-3OH Synthesis (PCL)-3OH and varying amounts of D,L-lactide and glycolide were added into a round-bottom flask under N2 and heated to 140° C. to melt the reaction contents. After melting, the temperature was reduced to 120° C. and stannous octoate was added. The reaction continued with stirring while monitoring the monomer conversion with H1 NMR and THF GPC. Once the reaction reaches the desired molecular weight, reaction contents were cooled to room temperature, dissolved in chloroform and precipitated into cold diethyl ether three times. The precipitate was dried under vacuum.

Example 6

(PCL-b-PLGA)-3MA Synthesis

Refer to Table 5 for an example of the molar ratio and masses of each reagent used to synthesize a 1 kg batch of (PLGA-b-PCL)-3MA.

(PCL-b-PLGA)-3OH was dissolved in anhydrous DCM in a round bottom flask under N2. Triethylamine (TEA) and a 400 ppm BHT were added the reaction flask and the reaction flask was cooled to 0° C. in an ice water bath. The reaction flask was equipped with a pressure-equalizing addition funnel that was charged with methacrylol chloride. Once the reaction flask reached 0° C., methacrylol chloride was added dropwise over 2 hours. The reaction proceeded for 12 h at 0° C. and then 24 h at room temperature. Once complete, the precipitate was removed via vacuum filtration. The filtrate was collected and DCM was removed with rotary evaporation. The resulting viscous oil was dissolved in THF and precipitated into cold methanol. The precipitate was dissolved in DCM and washed with aqueous HCL (3%, 2 times), saturated aqueous sodium bicarbonate solution, and saturated aqueous sodium chloride, then dried over magnesium sulfate. The magnesium sulfate was filtered off via vacuum filtration, and the filtrate was collected. DCM was removed via rotary evaporation and the solid product was collected and characterized with THF GPC, H1 NMR, FTIR, and DSC.

TABLE 5

Example of molar ratios and mass of each reagent needed to synthesize a 1 kg batch of (PLGA-b-PCL)-3MA.

| Reagent | Molecular Weight (g/mol) | Molar Ratio | Density (g/mol) | Mass (g) | Volume (mL) | Moles |
|---|---|---|---|---|---|---|
| (PLGA-b-PCL)-3OH | 6000 | 1 | — | 1000 | — | 0.17 |
| Methacrylol Chloride (MC) | 104.54 | 4.8 | 1.07 | 83.6 | 78.2 | 0.80 |
| Triethylamine (TEA) | 101.19 | 4.8 | 0.726 | 80.9 | 111.5 | 0.63 |
| Butylated hydroxy-toluene (BHT) | 220.35 | ~400 ppm | | 0.47 | | |
| Dichloromethane (DCM) | — | 0.2 g/mL | — | — | 5000 | — |

Example 7

Difunctional Oligomer Resin Formulation

The following ingredients were mixed together in the following weight percents to provide a light polymerizable resin for additive manufacturing:

(1) 66.2% of the difunctional oligomer prepared in Examples 1-3 above;

(2) 3.5% trimethylolpropane triacrylate (TMPTMA) reactive diluent;

(3) 28.4% of N-methyl pyrollidone (NMP) non-reactive diluent; and (4) 1.89% of Irgacure® 819 photoinitiator.

Example 8

Tri-Arm Oligomer Resin Formulation

The following ingredients were mixed together in the following weight percents to provide a light polymerizable resin for additive manufacturing:

(1) 68.6% of the tri-arm oligomer prepared in Examples 4-6 above;

(2) 29.4% of N-methyl pyrrolidone (NMP) non-reactive diluent; and (3) 1.96% of Irgacure® 819 photoinitiator.

Example 9

Additive Manufacturing and Post-Processing

With resins prepared as described in the examples above, additive manufacturing is carried out on a Carbon Inc. M1 or M2 apparatus, available from Carbon Inc., 1089 Mills Way, Redwood City California, 94063 in accordance with standard techniques.

When the resin contains a non-reactive diluent, the objects can experience a global shrinkage upon washing/extraction by the extent of the non-reactive diluent loading amount. Therefore, a dimensional scaling factor is applied to the part .stl file or 3MF file to enlarge the printed part and intentionally account for subsequent shrinkage during post processing steps.

Post processing of the produced parts can be carried out as follows: After removing the build platform from the apparatus, excess resin is wiped from flat surfaces around the objects, and the platform left on its side to drain for about 10 minutes. The objects are then dunk washed in acetone 3 times, with a 30 second dunk in acetone followed by five minutes of drying for each dunk. After the third dunk, the parts are allowed to dry for 20 minutes, and then flood cured for 20 seconds, while still on the build platform, in a DYMAX ultraviolet flood curing apparatus. The parts are then removed from their build platform, placed face down on a polytetrafluoroethylene such as TEFLON® polymer block, and flood cured for 20 seconds in the DYMAX.

Next, residual non-reactive diluent (e.g. N-methyl pyrrolidone) is extracted from the parts by immersing in acetone and shaking at 37° C. overnight. The solvent is exchanged once in the middle of the extraction (approximately 8 hours after start). The objects are then removed from the acetone and vacuum dried overnight at 60° C. overnight. The parts are then checked for residual NMP and, if no detectable residual, checked for tackiness. If the parts remain tacky, they are then flood cured under nitrogen in an LED based flood lamp (such as a PCU LED N2 flood lamp, available from Dreve Group, Unna, Germany).

The foregoing is illustrative of the present invention, and is not to be construed as limiting thereof. The invention is defined by the following claims, with equivalents of the claims to be included therein.

We claim:

1. An adhesion barrier comprising a sheet having a top surface and a bottom surface, said sheet comprising interconnected, vertically aligned, partitions, said partitions forming pores, said pores extending from said top surface through said bottom surface, wherein said sheet is comprised of a flexible or elastic polymer, wherein said sheet is produced from a light polymerizable resin by an additive manufacturing process, wherein said sheet has a thickness of at least 1 millimeter, wherein said flexible or elastic polymer comprises a bioresorbable polyester, and wherein:

said sheet has a length (X) dimension, a width (Y) dimension, and a depth (or vertical) (Z) dimension, said length and width dimensions together comprising lateral dimensions; and said sheet is stiffer in said vertical dimension than in said lateral dimensions.

2. The adhesion barrier of claim 1, wherein:

said pores have an average diameter of 0.05 millimeters to 2 millimeters; and/or said partitions have an average thickness of 0.1 millimeters to 2 millimeters.

3. The adhesion barrier of claim 1, wherein said partitions are curved, planar, or a combination thereof when viewed from above the top surface or below the bottom surface.

4. The adhesion barrier of claim 1, wherein said additive manufacturing process comprises bottom up or top down stereolithography.

5. The adhesion barrier of claim 1, wherein the adhesion barrier is prepared by photopolymerization of said resin comprising or consisting essentially of:

(a) from 5 percent by weight to 90 percent by weight of (meth)acrylate terminated bioresorbable polyester oligomer;

(b) from 1 percent by weight to 70 percent by weight of non-reactive diluent;

(c) from 0.1 percent by weight to 4 percent by weight of photoinitiator;

(d) optionally, from 1 percent by weight to 50 percent by weight of reactive diluent; and (e) optionally, from 1 percent by weight to 50 percent by weight of filler.

6. The adhesion barrier of claim 5, wherein said oligomer comprises a linear oligomer.

7. The adhesion barrier of claim 5, wherein said oligomer comprises a branched oligomer.

8. The adhesion barrier of claim 5, wherein said oligomer comprises degradable ester linkages between constituents selected from caprolactone, lactide, glycolide and dioxanone monomers in an ABA block, BAB block, CBC block, BCB block, AB random composition, BC random composition, or any combination thereof, wherein:

A=poly(lactide) (PLA), poly(glycolide) (PGA), poly(lactide-co-glycolide) (PLGA), or any combination thereof, B=polycaprolactone (PCL), and C=polydioxanone (PDX).

9. The adhesion barrier of claim 8, wherein said oligomer comprises an ABA block or a CBC block in linear and/or branched form.

10. The adhesion barrier of claim 9, wherein A is:

(i) poly(lactide);

(ii) poly(glycolide);

(iii) poly(lactide-co-glycolide) containing lactide and glycolide in a molar ratio of either 90:10 to 55:45 lactide:glycolide (i.e., a lactide rich ratio) or 45:55 to 10:90 lactide:glycolide (i.e., a glycolide rich ratio);

or any combination of the foregoing.

11. The adhesion barrier of claim 8, wherein:

A (PLA, PGA, PLGA, or a combination thereof) has a molecular weight (Mn) of from 1,000 daltons to 10,000 daltons; and B (PCL) has a molecular weight (Mn) of from 1,000 daltons to 10,000 daltons.

12. The adhesion barrier of claim 5, wherein said oligomer has a molecular weight (Mn) of from 2 kilodaltons to 20 kilodaltons.

13. The adhesion barrier of claim 5, wherein said non-reactive diluent is selected from the group consisting of dimethylformamide, dimethylacetamide, N-methyl pyrrolidone (NMP), dimethyl sulfoxide, cyclic carbonate, diethyl adipate, methyl ether ketone, ethyl alcohol, acetone, and combinations thereof.

14. The adhesion barrier of claim 5, wherein said non-reactive diluent is propylene carbonate.

15. The adhesion barrier of claim 5, wherein said reactive diluent comprises an acrylate, a methacrylate, a styrene, a vinylamide, a vinyl ether, a vinyl ester, polymers containing any one or more of the foregoing, or a combination of two or more of the foregoing.

16. The adhesion barrier of claim 5, wherein the adhesion barrier and/or resin further comprises at least one additional ingredient selected from: pigments, dyes, active compounds or pharmaceutical compounds, and detectable compounds, and combinations thereof.

17. The adhesion barrier of claim 5, wherein the adhesion barrier and/or resin further comprises a filler.

18. The adhesion barrier of claim 1, wherein the adhesion barrier is prepared by photopolymerization of said resin consisting essentially of:

(a) from 5 percent by weight to 90 percent by weight of a (meth)acrylate terminated, linear or branched, bioresorbable polyester oligomer of monomers in an ABA block or CBC block, wherein:

A is poly(lactide) (PLA), poly(glycolide) (PGA), poly(lactide-co-glycolide) (PLGA), or a combination thereof, with said PLGA containing lactide and glycolide in a molar ratio of either 90:10 to 60:40 lactide:glycolide (i.e., a lactide rich ratio) or 40:60 to 10:90 lactide:glycolide (i.e., a glycolide rich ratio), and A has a molecular weight (Mn) of from 1,000 daltons to 10,000 daltons;

B is polycaprolactone (PCL) and has a molecular weight (Mn) of from 1,000 daltons to 10,000 daltons; and C is polydioxanone (PDX) and has a molecular weight (Mn) of from 1,000 daltons to 10,000 daltons and (b) from 1 percent by weight to 70 percent by weight of propylene carbonate;

(c) from 0.1 percent by weight to 4 percent by weight of photoinitiator, (d) optionally, from 1 percent by weight to 50 percent by weight of reactive diluent; and

(e) optionally, from 1 percent by weight to 50 percent by weight of filler.

19. The adhesion barrier of claim 1, wherein said adhesion barrier is produced by photopolymerizing said resin in the shape of the adhesion barrier.

20. A method of making an adhesion barrier of claim 1, comprising producing said adhesion barrier by photopolymerizing said resin in the shape of the adhesion barrier.

21. The method of claim 20, further comprising cleaning said adhesion barrier after said producing step.

22. The method of claim 20, further comprising exposing said adhesion barrier to additional light after said producing step to further react unpolymerized constituents therein.

23. The method of claim 20, further comprising extracting residual diluent from said adhesion barrier after said producing step.

24. The method of claim 20, further comprising drying said adhesion barrier to remove extraction solvents therefrom.

25. The method of claim 20, further comprising producing said adhesion barrier in enlarged form to offset shrinkage of said adhesion barrier that occurs during said extracting, further exposing, and/or cleaning steps, and drying steps.

* * * * *